(12) United States Patent
Chang et al.

(10) Patent No.: US 6,596,521 B1
(45) Date of Patent: Jul. 22, 2003

(54) METHOD FOR MANUFACTURING ORGANIC ACID BY HIGH-EFFICIENCY CONTINUOUS FERMENTATION

(75) Inventors: Ho Nam Chang, Taejon (KR); Yong Keun Chang, Taejon (KR); Sun Hoon Kwon, Taejon (KR); Woo Gi Lee, Taejon (KR); Pyung Cheon Lee, Taejon (KR); Ik Keun Yoo, Seoul (KR); Seong Jin Lim, Taejon (KR)

(73) Assignee: Korea Advanced Institute of Science and Technology, Taejeon (KR)

( * ) Notice: Subject to any disclaimer, the term of this patent is extended or adjusted under 35 U.S.C. 154(b) by 0 days.

(21) Appl. No.: 09/529,570

(22) Filed: Apr. 13, 2000

(30) Foreign Application Priority Data

Apr. 13, 1999 (KR) .............................. 99-13041

(51) Int. Cl.$^7$ .............................. C12P 7/40; C12P 7/56; C12P 7/44; C12M 1/00
(52) U.S. Cl. .................. 435/136; 435/139; 435/142; 435/144; 435/145; 435/294.1; 435/383
(58) Field of Search ................... 435/383, 139, 435/294.1, 136, 142, 144, 145

(56) References Cited

PUBLICATIONS

Aeschlimann, A. and U. von Stockar, *Enzyme Microb. Technol.*, 13:811–816 (1991), "Continuous Production of Lactic Acid from Whey Permeate by *Lactobacillus helveticus* in a Cell–Recycle Reactor."

Aeschlimann, A., and U. von Stockar, *Appl. Microbiol. Biotechnol.*, 32:398–402 (1990), "The Effect of Yeast Extract Supplementation on the Production of Lactic Acid from Whey Permeate by *Lactobacillus helveticus*."

Bibal, Bernard, et al., *Biotechnology and Bioengineering*, 37:746–754 (1991), "High–Concentration Cultivation of *Lactococcus cremoris* in a Cell–Recycle Reactor."

Bruno–Bárcena, J. M., et al., *Appl. Microbiol. Biotechnol.*, 51:316–324 (1999), "Continuous Production of L(+)–Lactic Acid by *Lactobacillus casei* in Two–stage Systems."

Chiarini, Luigi, et al., *Appl. Microbiol. Biotechnol.*, 36:461–464 (1992), "Influence of Growth Supplements on Lactic Acid Production in Whey Ultrafiltrate by *Lactobacillus helveticus*."

Nielsen, Jens, et al., *Biotechnology and Bioengineering*, 38:1–10 (1991), "Structured Modeling of a Microbial System: I. A Theoretical Study of Lactic Acid Fermentation."

Nishiwaki, A., and I. J. Dunn, *Bioprocess Engineering*, 21:299–305 (1999), "Performance of a Two–Stage Fermentor with Cell Recycle for Continuous Production of Lactic Acid."

Ohashi, Ryo, et al., *Journal of Bioscience and Bioengineering*, 87(5):647–654 (1999), "Continuous Production of Lactic Acid from Molasses by Perfusion Culture of *Lactococcus lactis* Using a Stirred Ceramic Membrane Reactor."

Øyaas, J., et al., *Appl. Microbiol. Biotechnol.*, 46:240–249 (1996), "Uptake of Lactose and Continuous Lactic Acid Fermentation by Entrapped Non–Growing *Lactobacillus helveticus* in Whey Permeate."

Planas, J., et al., *Appl. Microbiol. Biotechnol.*, 45:737–743 (1996), "Enhanced Production of Lactic Acid through the Use of a Novel Aqueous Two–Phase System as an Extractive Fermentation System."

*Primary Examiner*—Herbert J. Lilling
(74) *Attorney, Agent, or Firm*—Knobbe, Martens, Olson & Bear LLP.

(57) ABSTRACT

The present invention provides a method for manufacturing organic acid by high-efficiency fermentation, which comprises the steps of continuous culture of organic acid bacteria and collection of organic acid produced from the culture employing a cell-recycle multiple-stage continuous fermentor with serially connected fermentors, each of which comprises a fermentor containing a ferment container, temperature controller, stirrer, and pH controller; pumps for efflux-circulation of media from the fermentor; and, cell separator for separation and circulation of media from the pumps. According to the present method, the high-concentration lactic acid of 90 g/L can be produced with the high productivity of 50 g/L/h, which can reduce the facility cost and production cost in the bulk manufacturing process. In addition, the present invention can be effectively applied to the production of other organic acids such as acetic acid, formic acid, citric acid, malic acid, maleic acid, fumaric acid, and succinic acid, which show the end-product inhibition.

24 Claims, 4 Drawing Sheets

METHOD FOR MANUFACTURING ORGANIC ACID BY HIGH-EFFICIENCY CONTINUOUS FERMENTATION

FIELD OF THE INVENTION

The present invention relates to a method for manufacturing organic acid by high-efficiency fermentation, more specifically, to a method for manufacturing organic acid in a highly efficient manner by culturing organic acid bacteria in a cell-recycle multiple-stage continuous fermentor.

BACKGROUND OF THE INVENTION

Organic acids such as lactic acid, acetic acid, and citric acid which are widely used in industry have been manufactured by chemical synthesis, enzyme reaction or microbial fermentation process. However the cost-efficiency problem has limited the availability of manufacturing processes other than chemical synthesis, and lots of efforts have been made to replace the chemical process with more environment-friendly fermentation process. The importance of new process has been stressed by the discovery of microorganisms capable of producing organic acids, the development of high-efficiency fermentation process, and the spreading of the cognition about environmental problems. Although the fermentation technology is usually employed in the manufacturing process for acetic acid and citric acid, relatively low yield for other organic acids has limited, or sometimes banned, the practical use of fermentation process (see: Roehr, M., Products of Primary Metabolism, in: Biotechnology, $2^{nd}$ Ed., Vol. 6(Rehm, H,-J., Reed, G., Eds.), Weinheim: Verlag Chemie, 1996).

Naturally, a variety of approaches have been made to establish a fermentation process for a very important organic acid of lactic acid whose physical properties and fermentation conditions have been known, and to connect the result of lactic acid production fermentation with those of other organic acids. In line with these activities, lactic acid fermentation using naturally abundant materials such as starch, glucose, sugar and lactose has consistently increased and high-efficiency fermentation process has been sought to meet the enormous potential need, while the chemical synthesis of lactic acid has gradually decreased.

Lactic acids which are produced in the metabolic pathway of living organisms, are contained in numerous fermented foods such as Kimchi (a Korean traditional fermented product) and Yakult. The lactic acids have been manufactured mainly in U.S.A. and European contries since its first identification by Scheele in 1780. Lactic acid which is optically active, due to a chiral carbon, is classified as L- and D-lactic acids, and humans are able to utilize only L-form. Lactic acids are produced by microbial fermentation in a form of L- or D-lactic acid, sometimes racemic mixture of the two forms, depending on the specificity of enzymes of the microorganisms.

Though the world market of lactic acid in the fields of foodstuff and cosmetics is somewhat limited, new demands in the biodegradable polymers and diverse solvents have rapidly grown. To meet the needs in the art, it is essentially required to manufacture lactic acid by a novel, high-efficiency method, compared to the conventional processes. Lactic acid-based biopolymer can be degraded easily under the environmental condition, and has good properties in light of mechanical stability, which makes plausible the use of lactic acid as a base material for polymer synthesis.

Until now, lactic acid has been manufactured by employing the batch-type fermentation process which comprises the steps of culturing lactic acid bacteria for more than 60 hours after inoculation and isolating lactic acid from the culture medium. The batch process has an advantage of high-concentration lactic acid production of over 120 g/L, though it has revealed a critical shortcoming of low volumetric productivity of less than 5 g/L/h. To compensate for the low productivity, the fermentation volume is enlarged, which in turn increases the cost for the construction of fermentation facilities and the maintenance of the facilities.

As an alternative approach to overcome the low productivity of batch-type fermentation process, cell-recycling method by which microorganisms are concentrated in a fermentor to increase the productivity, has been suggested in the art. This method employs the principle that the concentration of the enzyme for lactic acid synthesis increases as the cell density in the fermentor does, which comprises the steps of: maintaining lactic acid bacteria in a fermentor by using isolation techniques such as centrifugation and membrane separation; culturing the lactic acid bacteria in a medium containing sugar as a major component; and, collecting the culture containing lactic acid.

Cell-recycling method using membrane separation has been studied in the U.S.A. since 1980's, and in 1987, Cheryan et al reported that the volumetric lactic acid productivity of 84 g/L/h and the lactic acid concentration of 117 g/L can be realized (see: Mehaia, M. A. and M. Cheryan, Process Biochemistry, December 185–188, 1987). Cheryan et al also successfully obtained the volumetric lactic acid productivity of 22 g/L/h and the lactic acid concentration of 89 g/L (see: Tejayadi, S. and M. Cheryan, *Appl. Microbiol. Biotechnol.*, 43:242–248, 1995). However, the prior art method is proven to be less satisfactory in a sense that the said results is not reproducible under the normal condition for continuous fermentation (see: Timmer, J. M. and J. Kromkamp, FEMS Microbiology Reviews, 14:29–38, 1994). Therefore, the productivity of 22 g/L/h and the concentration of 89 g/L of lactic acid ferment has been known to be the highest efficiency and concentration among the Cheryan's results in 1995.

Although many results have been published using cell-recycling method in the continuous-type fermentation of lactic acid, Cheryan et al's result is distinguished from the others in light of the high concentration of over 90 g/L of lactic acid ferment. The difficulty in obtaining high concentration of lactic acid is caused by the severe end-product inhibition, which is brought about at the lactic acid concentration of over 50 g/L.

On the other hand, multiple-stage continuous fermentation has been developed to attenuate the end-product inhibition in the course of lactic acid fermentation, in which the steps of culturing microorganisms and producing lactic acid are separated to give a high productivity: That is, using a multiple-stage continuous fermentor with two or more fermentors serially connected with each other, bacterial growth was facilitated in the first fermentor containing a relatively low concentration of target product to maintain the lactic acid production rate of the microorganism, and the target product was manufactured in the subsequent fermentors to reach the desired high concentration.

Actually, the multiple-stage continuous fermentation comprising two or 10 stages has been reported to allow the high-efficiency production of ethanol, a typical product showing the end-product inhibition, and it could be applied in other cases such as lactic acid, monoclonal antibody, enzyme and liquor as well (see: Gooijer, C. D., et al, *Enzyme-Micorb. Technol.*, 18:202–219, 1996). Based on the perception about the end-product inhibition of lactic acid, which shows the same phenomenon as in ethanol, Mulligan et al performed two- and three-stages of continuous fermentation and improved the productivity of lactic acid by 25% and 57%, compared to single-stage method, respectively. However, the productivity of Mulligan et al's was relatively low (e.g., 3~5 g/L/h), due to low cell concentration of 2~3 g/L (see: Mulligan, C. N., and B. F. Safi, *Biotechnol. Bioeng.*, 38:1173, 1991).

Under these circumstances, many attempts have been made to produce lactic acid with a high-efficiency, by combining the cell-recycling method and the multiple-stage continuous fermentation method. However, it has revealed a problem that the production efficiency is not improved any more, compared to the chemical synthesis and batch-type fermentation. Accordingly, methods for manufacturing lactic acid with a high concentration and efficiency have been actively studied in the art, since the high efficiency production of lactic acid can be applied to the other organic acids such as acetic acid, formic acid, citric acid, malic acid, maleic acid, fumaric acid and succinic acid.

Nabisco Brands Inc. used serially connected two-stage fermentors to increase the final concentration of acetic acid and membranes between the said two fermentors in order to concentrate microorganisms in each fermentor (see: U.S. Pat. No. 4,456,622). However, it turned out to be a single fermentor in which two batch-type fermentors are connected with each other simply to reuse the microorganisms after fermentation. Accordingly, acetic acid cannot be produced with a high concentration and productivity, compared to the chemical synthesis.

Therefore, needs have continued to exist for the development of a novel method for manufacturing lactic acid in a highly efficient manner, which can be applied to the production of other organic acids.

SUMMARY OF THE INVENTION

The present inventors have tried to establish an improved method for manufacturing highly concentrated lactic acid by high-efficiency fermentation by employing a cell-recycle multiple-stage continuous fermentor with two-stage serially connected fermentors, and found that lactic acid can be manufactured with a high concentration of over 90 g/L and productivity of over 50 g/L/h, which can be effectively applied to the other organic acid fermentation processes showing the end-product inhibition.

A primary object of the present invention is, therefore, to provide a method for manufacturing organic acid with a high concentration and productivity.

The other object of the invention is to provide a cell-recycle multiple-stage continuous fermentor with serially connected fermentors.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

Figure 1:
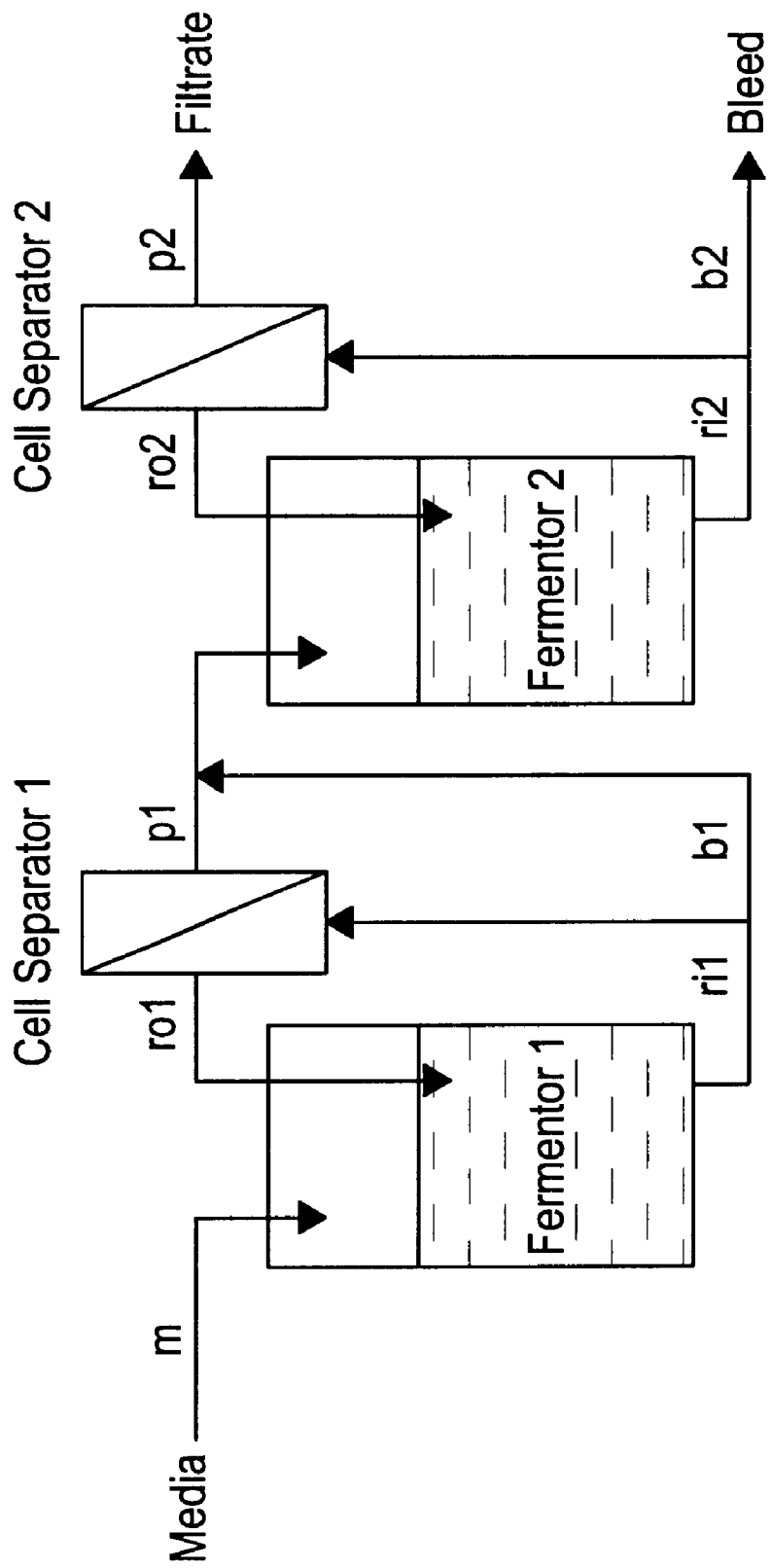
FIG. 1 is a schematic diagram depicting the structure of cell-recycle two-stage continuous fermentator of the present invention.

A method for manufacturing organic acid by high-efficiency fermentation of the present invention, comprises the steps of: continuous culture of organic acid bacteria and collection of the organic acid produced from the culture, employing a cell-recycle multiple-stage continuous fermentor with cell-recycle device and serially connected fermentors.

The cell-recycle device comprises cell separator and pumps, and the cell separator includes centrifuger or membrane separator, more preferably membrane separator, to separate the microorganism from the growth media and fermentation product. Ultrafiltration membrane is the most suitable means for cell separation among the reverse osmosis membrane, ultrafiltration membrane, and microfiltration membrane, because of the disadvantages of other membrane: Reverse osmosis membrane has a relatively low filtration capacity. Microfiltration, despite of its high filtration capacity, has a demerit of the rapid downfall of performance due to the clogging with microorganism in the ferment and/or medium component(s). In order to maintain the high filtration capacity of microfiltration, two filters are operated in turn, and during the resting time of one filter, the traces on the other filter should be washed out. In case of the ultrafiltration membrane, despite the low filtration capacity, it has an advantage of allowing longer time operation.

Since the media feeding, the ferment removal, the cell separation and the cell-recycle occur simultaneously in the cell-recycle device of the invention, the flux controlling pumps are needed, such as peristaltic pumps, membrane pumps, gear pumps or combined forms of them. Pumps are positioned in front of and in the back of continuous fermentors and cell separators, or between continuous fermentors and cell separators. The functions of the pumps are to add the medium to the fermentor, to circulate the ferment outside the fermentor, or to remove the ferment from the fermentor. The continuous fermentors can be connected for 2 to 6 stages depending on the characteristics of target product.

Each of the serially connected fermentor comprises a fermentor, temperature controller, stirrer, pH controller, and optionally the gas injector (if a gas is needed for the growth of the microorganism or the product formation). In case of the lactic acid bacteria, it is not necessary to inject additional gas due to the anaerobic condition for the culture. But, nitrogen gas may be injected to fermentors to guarantee the complete anaerobic condition, which may be critical for other organic acid bacteria. Furthermore, acid or base in the form of solution or gas may be added into the fermentor to control the pH of the ferment.

For serial connection of the cell-recycle fermentors, the filtrated ferment from the cell-recycle device was inputted into the second fermentor under the control of influx, and bleed removing the microorganism from the ferment was inputted into the second fermentor under the control of influx, to maintain the high-concentration continuous fermentation. The ferment was also recycled or bleeded in the second fermentor, using the cell-recycle device, to realize the high-efficiency production of high-concentration organic acid. During the cell-recycle multiple-stage continuous fermentation, the organic acid bacteria are maintained in the fermentor with a high-concentration, by the continuous recycling of the microorganisms with the cell seperator, and the fermentation media consisting of sugars, such as glucose, lactose, sucrose, or starch, as major components may be added to the ferment from the outside. The optimal condition for organic acid fermentation can be maintained by preventing the increase of the cell concentration by the aid of pumps for removing a small portion of microorganism-containing ferment, and the decrease of fermentation efficiency by the aid of pump for removing microorganism-free ferment to the outside, respectively.

The method of the present invention is further illustrated in the following description on the cell-recycle multiple-stage continuous fermentor and operation thereof.

1. Cell-recycle Multiple-stage Continuous Fermentor

Figure 2:
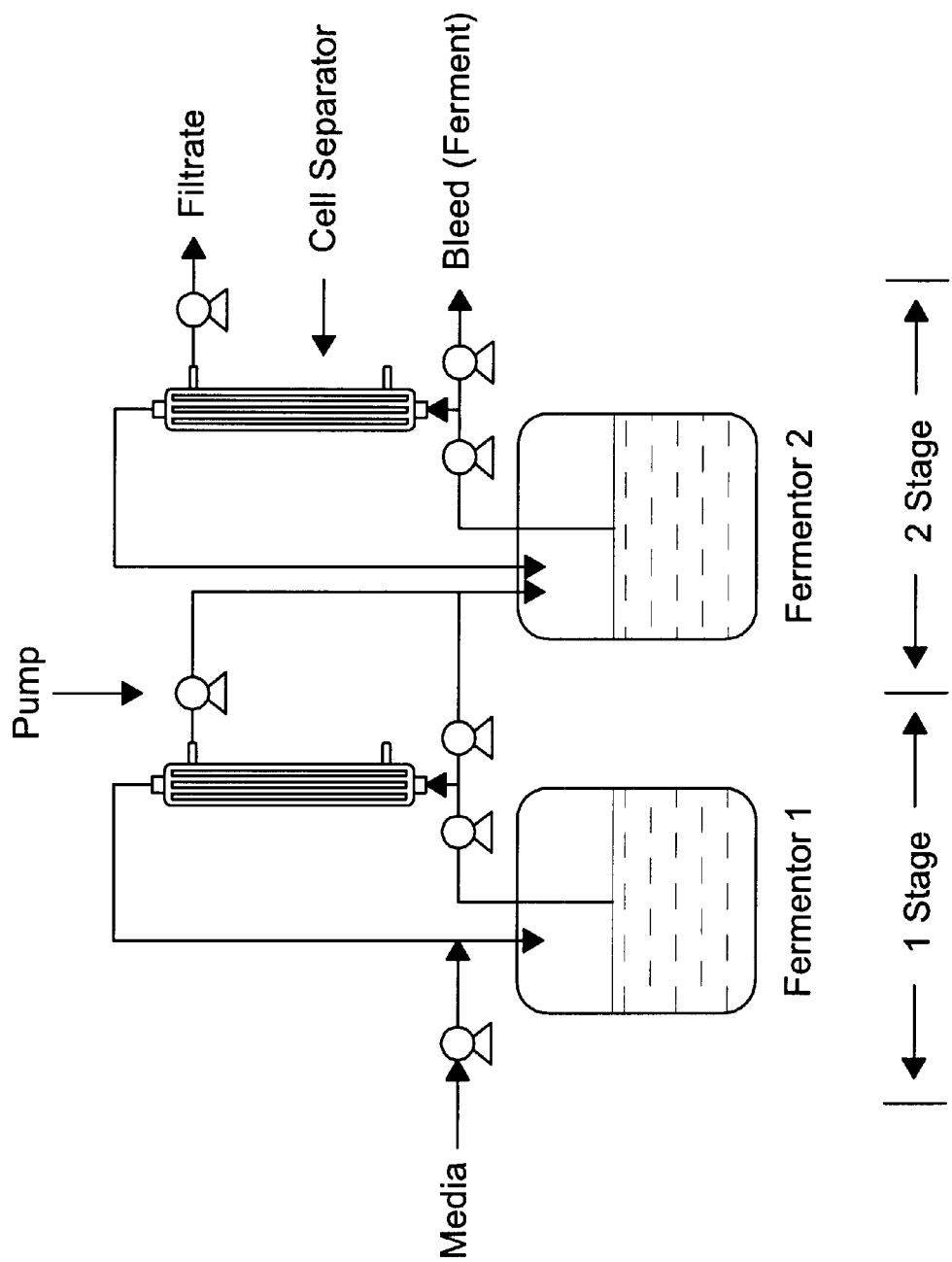
FIG. 2 is a schematic diagram depicting the assembly of cell separator and pump in the cell-recycle two-stage continuous fermentator.

Cell-recycle device equipped with cell separator and pumps is used to increase the concentration of microorganism in a continuous fermentor. The microorganisms are separated and recycled in the fermentor, while the ferment containing the produced lactic acid and remaining media components are filtered and guided into the second continuous fermentor. By carrying out the multiple-stage continuous fermentation, the microorganisms are successively concentrated, though the performance of the pumps and the cell separator is lowered. Therefore, the ferment should be bleeded in a constant rate and inputted to the second fermentor together with the filtered ferment. By way of bleeding, the microorganism concentration increases to a high level and reaches to the steady state, and the culturing can be successively proceeded in the second continuous fermentor, and the cell concentration is persistently maintained by the filtration device having the same function as in the previous stage (see: FIG. 1). In FIG. 1, (m) represents the medium injected from the outside; (ri1) and (ro1) the cell-recycle in the first-stage; (b1) the bleed in the first-stage; (p1) the path of filtrate in the first-stage; (ri2) and (ro2) the cell-recycle in the second-stage; (b2) the bleed in the second-stage; and, (p2) the path of filtrate in the second stage, respectively. As can be seen in FIG. 1, more than two stages of fermentors can be connected with a cell-recycle multiple-stage continuous fermentor in a serial manner, each of which is equipped with cell separator to filtrate the ferment and pumps for removing the microorganism-containing ferment (b1 and b2) to maintain high-level of cell concentration. In addition, pumps play a role in medium injection (m), cell-recycling (ri1 and ri2) and filtrate flow-control (p1 and p2) (see: FIG. 2). The basic fermentation conditions such as temperature and pH, are regulated by a controller positioned in each continuous fermentor. Pumps for the addition of ammonia water may be provided in the fermentor to control the pH.

In order to produce the organic acid continuously and consistently using the said cell-recycle multiple-stage continuous fermentor, the long-time operation should be achieved under the constant fermentation volume, concentration of microorganisms and fermentation substrate, to reach a steady state of the continuous fermentation.

2. Operation

As fully described earlier, the operation factors, which are critical at each fermentation stage in the cell-recycle multiple-stage continuous fermentation, include fermentation volume, flow-rate of media and bleed rate of microoganisms. The appropriate ranges for these factors can be optimized from the simulation study, though it should be verified through the real experiments. The highest productivity of highly concentrated organic acid can be achieved with the smallest fermentation volume under the optimized condition. In this regard, the present inventors performed the cell-recycle continuous fermentation with serially connected two-stage continuous fermentors, together with the simulation study. In the two-stage continuous fermentor, fermentation volume ratio, media flow-rate and bleed rate of microorganisms are controlled by the conversion of dilution rate (D, final flow-rate/total fermentation volume) and bleed ratio (bleed rate/dilution rate). As a result, it was determined that the optimized conditions for the lactic acid production with a high concentration and high productivity are: the dilution rate of 0.3 to 0.7 $h^{-1}$, the bleed ratio of 0.01 to 0.1 in each stage, and the fermentation volume rate of 10:1 to 0.3:1, respectively.

The serial connection of two-stage continuous fermentors increased the productivity of lactic acid by 100% or more, when compared with Cheryan et al's results in 1995, indicating that the present method is more improved in terms of the efficiency than those of single-stage continuous fermentation, the batch fermentation or the chemical synthesis. In addition, the high-efficiency production of other organic acids can be realized by applying the cell-recycle multiple-stage continuous fermentor to the production of other organic acids showing the end-product inhibition, such as acetic acid, formic acid, citric acid, malic aci, maleic acid, fumaric acid or succinic acid.

The present invention is further illustrated in the following examples, which should not be taken to limit the scope of the invention. In particular, the method for manufacturing organic acid by high-efficiency fermentation of the present invention can be applied not only to the lactic acid illustrated in the examples, but also other organic acids showing the end-product inhibition. Accordingly, the present invention covers all of the methods for manufacturing organic acids including lactic acid by employing the cell-recycle multiple-stage continuous fermentor.

EXAMPLE 1

Batch-type Fermentation

Figure 3:
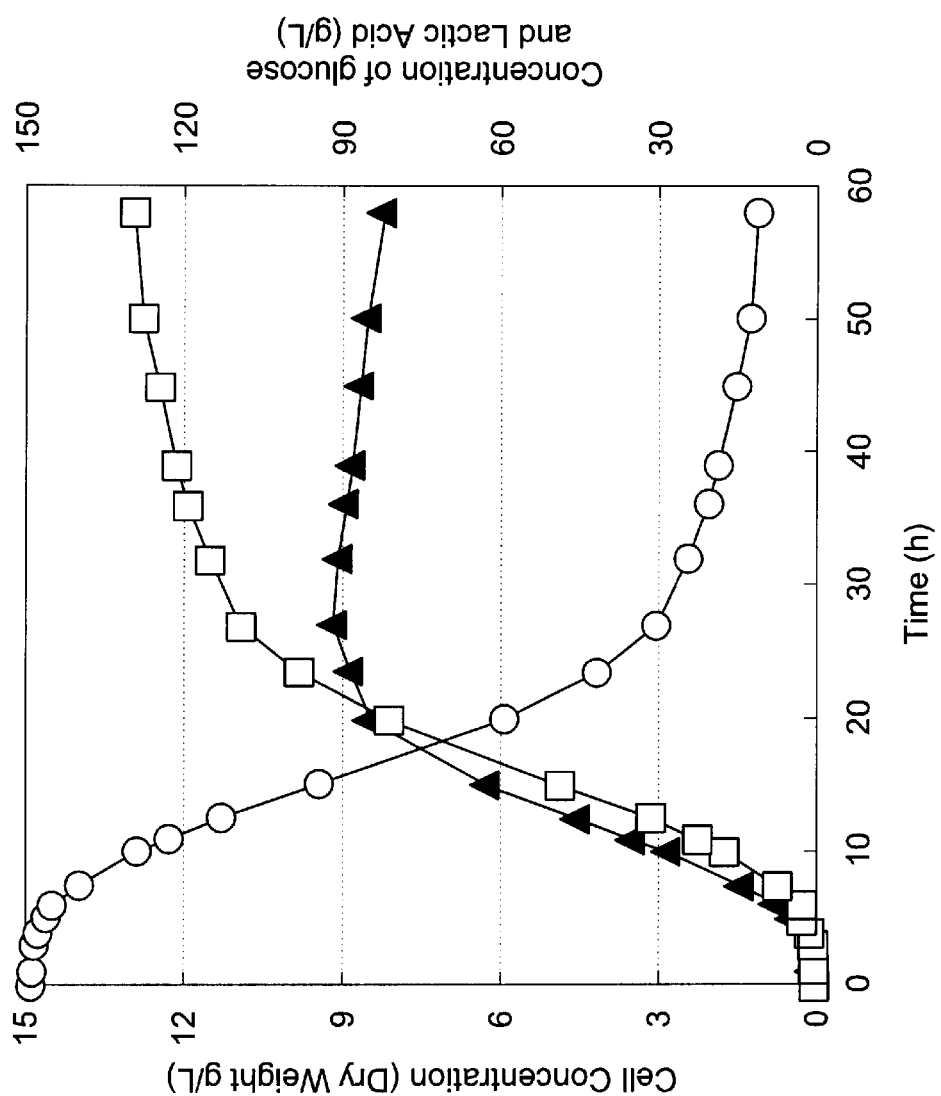
FIG. 3 is a graph showing the characteristics of batch-type lactic acid fermentation.

Batch-type fermentation was performed in order to examine the productivity and concentration of lactic acid by employing lactic acid bacteria of *Lactobacillus rhamnosus* (ATCC 108863): 1 ml aliquots of *L. rhamnosus* in glycorol-containing MRS (Difco, USA) were stored at −70° C. for later use as seeds. The media for batch fermentation contain 150 g/L of glucose, 15 g/L of yeast extract (Difco, USA), 2.5 g/L of $KH_2PO_4$, 0.5 g/L of $Na_3$-citrate.$2H_2O$, 0.2 g/L of $MgSO_4.7H_2O$, 0.03 g/L of $MnSO_4.H_2O$, 0.03 g/L of $FeSO_4.7H_2O$, 0.03 g/L of $ZnSO_4.7H_2O$, and 0.015 ml/L of $H_2SO_4$. Seeds were inoculated in 100 ml of MRS media, cultured for 12 hours while shaking, and the cultured media were transferred to 2 L fermentor. Then, ammonia water was added to the fermentation media to neutralize the lactic acid produced during the fermentation to reach at pH 6.0. and the fermentation was performed at a constant temperature of 42° C. The cell concentration in the ferment was obtained by the conversion of OD 620 mm value measured in the spectrophotometer (Ultraspec-300, Pharmacia, England), after dilution of ferment. The concentrations of glucose and lactic acid in the ferment were measured by HPLC with RI detector, after centrifugation of the ferment and removal of the microorganism, where Aminex HPX-87H (Biorad, USA) was used as a HPLC column and 10 μl of 10 times diluted ferment was injected. The concentrations of cells, glucose, and lactic acid during the fermentation process were determined for 60 hours by the method described above (see: FIG. 3). In FIG. 3, (▲) represents cell concentration as a dry weight; (0) concentration of the glucose; and, (□) concentration of lactic acid. As shown in FIG. 3, the highest lactic acid concentration of 112 g/L was achieved in 60 hours of batch-type fermentation, where the volumetric productivity was 2.3 g/L/h.

EXAMPLE 2

Cell-recycle Single-Stage Continuous Fermentation

Cell-recycle single-stage continuous fermentation was performed in a ferment volume of 250 mL by employing hollow fiber ultrafiltration membrane (UFP-500-C-4A, A/G Technology, USA) in order to observe the improvement in terms of productivity and concentration of lactic acid, and compared with those of batch fermentation in Example 1. The fermentation was carried out under two conditions of the bleed ratio 0.042 and the dilution rate 0.62 $h^{-1}$ and, the bleed ratio 0.078 and the dilution rate 0.72 $h^{-1}$. The composition of the media was shown in Table 1.

TABLE 1

| Components | Concentration (g/L) |
| --- | --- |
| Yeast Extract | 18 |
| $Na_3$-citrate · $2H_2O$ | 1 |
| $K_2HPO_4$ | 0.7 |
| $KH_2PO_4$ | 0.3 |
| $MgSO_4 · 7H_2O$ | 0.2 |
| $MnSO_4 · H_2O$ | 0.03 |
| $FeSO_4 · 7H_2O$ | 0.03 |
| $ZnSO_4 · 7H_2O$ | 0.03 |
| $H_2SO_4$ | 0.015 |
| Glucose | 180 |

As a result, it was determined that the cell concentration was 120 and 90 g-DCW (dried cell weight)/L; and, the lactic acid productivity was 33 and 38 g of lactic acid/L/h, respectively. Although the values were higher than those of the batch fermentation, the concentration of lactic acid was lower than 50 g/L under the said two conditions, indicating that substantial improvement was not accomplished. Since the lactic acid production activity of the microorganism was decreased under the high lactic acid concentration of 50 g/L, the lactic acid concentration was not increased despite the high cell concentration of 120 g-DCW/L. From the above results, it could be concluded that, low level of dilution rate be maintained, or cell-recycle multiple-stage continuous fermentation be introduced, in order to produce high-concentration lactic acid.

EXAMPLE 3

Cell-recycle Two-Stage Continuous Fermentation

Figure 4:
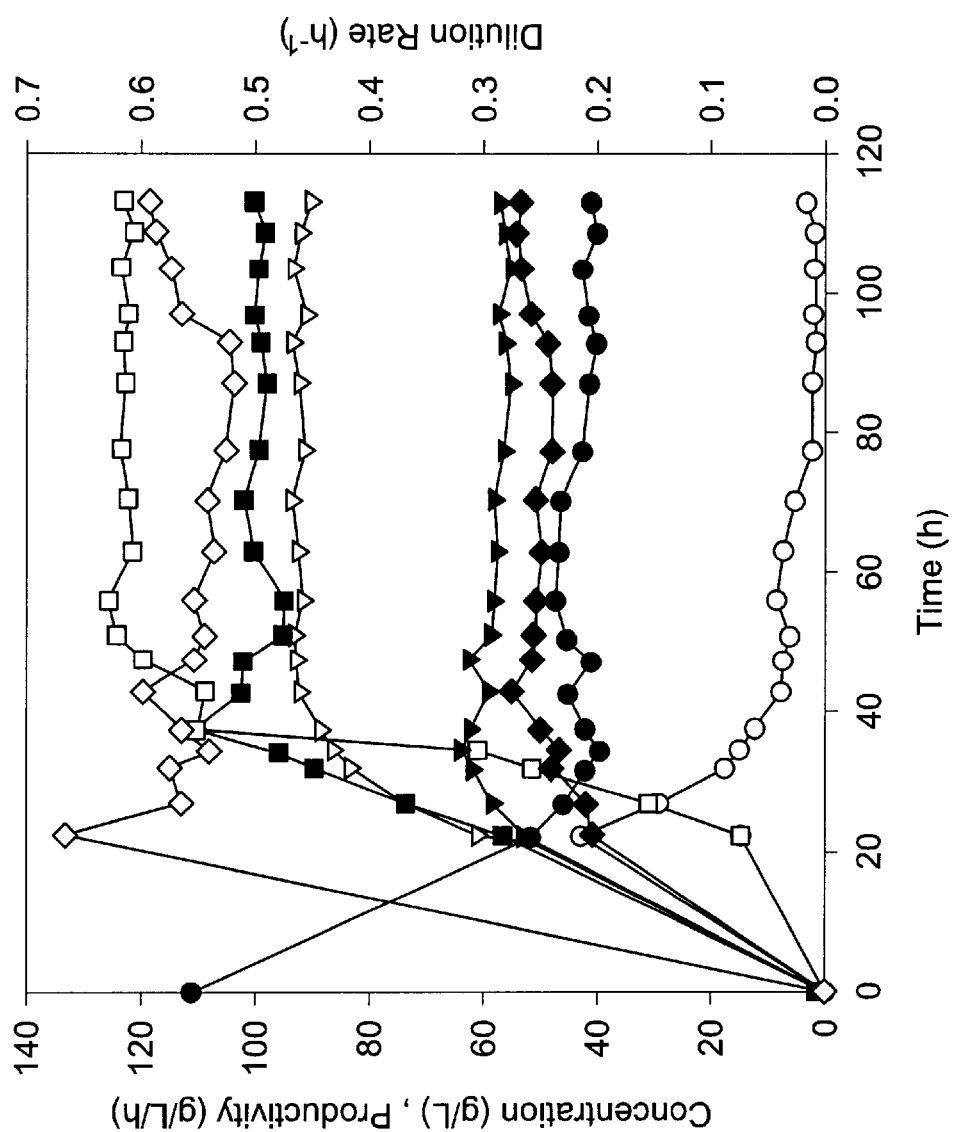
FIG. 4 is a graph showing the characteristics and productivity of lactic acid fermentation in a cell-recycle two-stage continuous fermentator.

The high productivity of lactic acid fermentatin was achieved by employing the cell-recycle multiple-stage continuous fermentator, much more than the batch fermentation or the cell-recycle single-stage fermentation: two continuous fermentors were connected with each other in a serial manner; the cell concentration in each fermentor was maintained over 100 g-DCW/L; the lactic acid concentrations in the first and second fermentors were maintained at the range of 40 to 60 g/L and, over 90 g/L, respectively. The ultrafiltration membranes of UFP-100H-6A (A/G Technology, USA) and Pellicon-2mini B-100V (Millipore Co., USA) were used, and the ferment volume of each fermentor was maintained at about 600 ml. The same media as in Example 2, except for using 105 g/L of glucose and 13 g/L of yeast extract, were continuously added. The bleed ratio was controlled in the range of 0.02 to 0.08, and the dilution rate 0.5 $h^{-1}$ to 0.6 $h^{-1}$. 45 hours of fermentation was enough to reach the steady state (see: FIG. 4). In FIG. 4, (●) means the concentration of glucose in the first continuous fermentor; (0) the concentration of glucose in the second continuous fermentor; (■) the cell concentration in the first continuous fermentor; (□) the cell concentration in the second continuous fermentor; (▼) the lactic acid concentration in the first continuous ferementor; (▽) the lactic acid concentration in the second continuous ferementor; (◇) the dilution rate in the fermentation; and, (◆) the productivity. As shown in FIG. 4, the concentration of the microorganism in each fermentor was maintained as high as 100 g-DCW/L, the final lactic acid concentration was over 90 g/L, and the lactic acid productivity was over 50 g/L/h. In this case, the concentration of remaining glucose was lower than 3 g/L, indicating that glucose was almost completely converted into lactic acid.

As clearly illustrated and demonstrated as above, the present invention provides a method for manufacturing lactic acid by high-efficiency fermentation employing a cell-recycle multiple-stage continuous fermentator with serially connected cell-recycle continuous fermentors. According to the present method, the high-concentration lactic acid of 90 g/L can be produced with the high productivity of 50 g/L/h, which is much higher than those of the conventional methods. In addition, the present invention can be effectively applied to the production of other organic acids such as acetic acid, formic acid, citric acid, malic acid, maleic acid, fumaric acid, and succinic acid, which show the end-product inhibition.

It will be apparent to those skilled in the art that certain changes and modifications can be made to this invention without departing from the spirit or scope of the invention as it is set forth herein.

What is claimed is:

1. A method of multi-stage fermentation comprising a plurality of unit fermentation processes, wherein at least one of the unit processes comprises:

feeding a fermentation medium into a container containing a microorganism producing an organic compound using the fermentation medium, whereby the container contains a fermentation mixture comprising the microorganism, the medium and the organic compound produced by the microorganism, taking a part of the fermentation mixture from the container;

separating the microorganism from the part of the fermentation mixture;

recycling the separated microorganism to the container;

collecting a filtrate; and wherein the medium fed into the container of each unit process comprises a filtrate collected from another unit process or a fresh fermentation medium.

2. The method of multi-stage fermentation as defined in claim 1, wherein the plurality of unit fermentation processes comprises two to six unit processes.

3. The method of multi-stage fermentation as defined in claim 2, wherein the multi-stage fermentation is carried out continuously.

4. The method of multi-stage fermentation as defined in claim 1, wherein a dilution rate (final flow rater/total fermentation volume) of the multi-stage fermentation is 0.3 to 0.7/hour.

5. The method of multi-stage fermentation as defined in claim 1, wherein a fermentation volume rate is 10:1 to 0.3:1.

6. The method of multi-stage fermentation as defined in claim 1, further comprising the step of bleeding a part of the fermentation mixture from the container used for one unit fermentation process.

7. The method of multi-stage fermentation as defined in claim 6, wherein the bled part of the fermentation mixture is fed into another container used for another unit fermentation process.

8. The method of multi-stage fermentation as defined in claim 7, wherein a bleed ratio (bleed rate/dilution rate) is 0.01 to 0.1.

9. The method of claim 1, wherein the filtrate collected from another unit process is the filtrate of the immediately preceding unit process.

10. The method of claim 1, wherein the fresh fermentation medium is fed to the very first unit process of the multi-stage fermentation.

11. The method of claim 1, wherein the organic compound comprises an organic acid.

12. The method of claim 11, wherein the organic acid is one selected from the group consisting of lactic acid, formic acid, citric acid, malic acid, maleic acid, fumaric acid and succinic acid.

13. The method of claim 1, wherein each unit process is carried out continuously.

14. The method of claim 1, further comprising separating the organic compound from the collected filtrate from the at least one of the unit processes.

15. The method of claim 1, wherein the separation of the microorganisms is conducted with use of a filter connected to the container such that the filter can continuously receive the fermentation mixture from the container at a flow rate and recycle the microorganisms to the container while allowing the filtrate to be collected.

16. The method of claim 15, wherein the filter comprises a centrifuge or a membrane selected from the group consisting of osmosis, ultrafiltration and microfiltration membranes.

17. The method of claim 1, wherein each unit process is conducted in a batch mode.

18. The method of claim 1, wherein at least one of temperature pH of the fermentation medium is controlled during the fermentation.

19. The method of claim 1, wherein the at least one of the unit process is conducted with use of a fermentor, which comprises:

the container adapted to receive the fermentation medium fed thereto and to contain microorganisms producing the organic compound using the fermentation medium, so that the container can contain the fermentation mixture; and a filter for separating the microorganisms from the fermentation mixture, the filter being connected to the container such that the filter can continuously receive the fermentation mixture from the container at a flow rate and recycle the microorganisms to the container while allowing the filtrate to be collected.

20. The method of claim 19, wherein the filter comprises a centrifuge or a membrane selected from the group consisting of osmosis, ultrafiltration and microfiltration membranes.

21. The method of claim 19, wherein, the fermentor further comprises at least one pump for feeding the medium to the container, a pump for transferring the fermentation mixture from the container to the filter, and a pump for recycling the microorganisms from the filter to the container.

22. The method of claim 19, wherein the container of the fermentor is fitted with a device chosen from the group consising of a temperature controller, a stirrer and a pH controller.

23. The method of claim 1, wherein the multi-stage fermentation is conducted with use of a multi-stage fermentor, which comprises a plurality of fermentation units, wherein the plurality of fermentation units are connected in cascade such that at least one of the fermentation unit of the cascade is adapted to receive a filtrate from the immediately preceding fermentation unit.

24. The method of claim 23, wherein the multi-stage fermentor further comprises a bleeding path between two neighboring fermentation units for allowing bleeding of the fermentation mixture from one having a lower concentration of the organic compound to the other having a higher concentration of the organic compound.

* * * * *